United States Patent [19]

Liav et al.

[11] Patent Number: 5,719,020
[45] Date of Patent: Feb. 17, 1998

[54] 4,7-DIALKOXY N-ACETYLNEURAMINIC ACID DERIVATIVES AND METHODS FOR DETECTION OF INFLUENZA TYPE A AND B VIRUSES IN CLINICAL SPECIMENS

[75] Inventors: Avraham Liav, Denver, Colo.; Joyce Anne Hansjergen; Craig David Shimasaki, both of Oklahoma City, Okla.

[73] Assignee: Oklahoma Medical Research Foundation, Oklahoma City, Okla.

[21] Appl. No.: 718,666

[22] Filed: Sep. 25, 1996

[51] Int. Cl.$^6$ .............................. C12Q 1/70; C12N 9/26; C07H 1/00; C07H 15/00
[52] U.S. Cl. .................. 435/5; 435/201; 536/1.11; 536/17.2; 536/18.6; 536/18.7
[58] Field of Search ................. 435/5, 201; 536/1.11, 536/17.2, 18.6, 18.7

[56] References Cited

U.S. PATENT DOCUMENTS

| | | | |
|---|---|---|---|
| 3,950,322 | 4/1976 | Thomas et al. | 260/210 R |
| 4,632,901 | 12/1986 | Valkirs et al. | 435/5 |
| 4,772,553 | 9/1988 | Fujii et al. | 435/13 |
| 4,810,636 | 3/1989 | Corey | 435/14 |
| 4,877,727 | 10/1989 | Miike et al. | 435/24 |
| 5,081,017 | 1/1992 | Longoria | 435/30 |
| 5,252,458 | 10/1993 | Liav et al. | 435/5 |
| 5,489,675 | 2/1996 | Sabesan | 536/17.2 |
| 5,556,963 | 9/1996 | Liav et al. | 536/55.3 |

FOREIGN PATENT DOCUMENTS

| | | | |
|---|---|---|---|
| WO 91/09972 | 7/1991 | WIPO. | |
| WO 91/16320 | 10/1991 | WIPO. | |
| WO 92/06691 | 4/1992 | WIPO. | |
| WO 96/04291 | 2/1996 | WIPO | C07H 15/04 |

OTHER PUBLICATIONS

Pachucki, "Early Detection of Influenza Virus by Using a Fluorometric Assay of Infected Tissue Culture", *J. of Clinical Microbiology*, vol. 26, No. 12 (Dec. 1988) pp. 2664–2666.

Yolken et al., "Fluorometric Assay for Measurement of Viral Neuraminidase—Application to the Rapid Detection of Influenza Virus in Nasal Wash Specimens", *J. of Infectious Diseases*, vol. 142, No. 4, (Oct. 1980) pp. 516–523.

Zbiral et al., "Synthesis of the 4-Methylumbelliferyl 2α-Glycosides of 7-Epi, 8-Epi-, and 7,8-Bis(epi)-N-acetylneuraminic Acids, as well as of 7-Deoxy-, 8-Deoxy, 9-Deoxy, and 4,7-Dideoxy-N-acetylneuraminic Acids and Their Bahaviour Towards Sialidase from Vibrio cholerae", *Liebigs, Ann. Chem.* (1989) pp. 519–526.

Zbiral et al., "Structural Transformations of N-Acetylneuraminic Acid, VII. Synthesis of 7-, 8-, 9-Desoxy- and 4,7-Didesoxyneuraminic Acid", *Monatshefte fur Chemie*, vol. 119 (1988) pp. 127–141.

Kim et al., "Enzymes in Carbohydrate Synthesis: N-Acetylneuraminic Acid Aldolase Catalyzed Reactions and Preparation of N-Acetyl-2-deoxy-D-neuraminic Acid Derivatives" *J. Am. Chem. Soc.*, vol. 110 (1988), pp. 6481–6486.

Kiyotani et al., "Enzymological Characteristics of Avian Influenza A Virus Neuraminidase" *Microbiol. Immunol.*, vol. 31, No. 11 (1987) pp. 1131–1135.

Kiyotani et al., "Enzymological Heterogeneity of Influenza B Virus Neuraminidase Demonstrated by the Fluorometric Assay Method", *Zbl. Bakt. Hyg.*, vol. (A260) (1985) pp. 273–285.

Kiyotani et al., "Fluorometric Measurement of Neuraminidase Activity of Influenza Viruses", *Hiroshima J. of Medical Sciences*, vol. 33, No. 2, pp. 287–292., 1984.

Yolken, "Enzyme Immunoassays for the Detection of Infectious Antigens in Body Fluids: Current Limitations and Future Prospects", *Review of Infectious Diseases*, vol. 4, No. 1 (1982) pp. 35–68.

Yolken, "Enzymic Analysis for Rapid Detection of Microbial Infection in Human Body Fluids: An Overview", *Clinical Chem.*, vol. 27, No. 9 (1981), pp. 1490–1498.

Myers et al. "The Synthesis of 4-Methylumbelliferyl α-Ketoside of N-Acetylneuraminic Acid and Its Use in a Fluorometric Assay for Neuraminidase", *Analytical Biochem.*, vol. 101, (1980), pp. 166–174.

Santer, "A Rapid Assay for Neuraminidase—The Detection of Two Differences in Activity Associated With Virus Transformation", *Biochimica et Biophysica Acta*, vol. 523, (1978) pp. 435–442.

Beau et al., "Metabolism of 4–O–Methyl–N–acetylneuraminic Acid a Synthetic Sialic Acid", *Eur. J. Biochem.*, vol. 106, (1980), pp. 4279–4283.

Gross et al., "Interaction of N-Acetyl–4–epi–D–neuraminic Acid with Key Enzymes of Sialic Acid Metabolism", *Biochemistry*, vol. 27, (1988) pp. 4279–4283.

(List continued on next page.)

*Primary Examiner*—Ardin H. Marschel
*Assistant Examiner*—Jezia Riley
*Attorney, Agent, or Firm*—Fitch, Even, Tabin & Flannery

[57] ABSTRACT

Chromogenic and fluorogenic 4,7-dialkoxy-N-acetylneuraminic acid substrates of the general formula

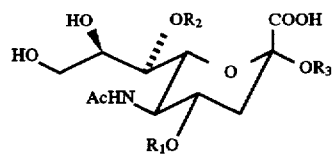

are provided wherein $R_1$ and $R_2$ are alkyl groups containing 1 to 4 carbon atoms and $R_3$ is a chromogenic or fluorogenic group. These substrates can be used to detect influenza types A and B in clinical samples or specimens. More particularly, these 4,7-dialkoxy-N-acetylneuraminic acid substrates can be used to distinguish between various viruses having neuraminidase reactivity. Thus, influenza type A and B viruses can be distinguished from parainfluenza type 1, 2, 3, and 4, and mumps using the 4,7-dialkoxy-N-acetylneuraminic acid derivatives of this invention. Diagnostic methods employing these substrates are provided to identify influenza type A and B viruses in clinical specimens and to distinguish from other viruses having neuraminidase reactivity.

21 Claims, No Drawings

OTHER PUBLICATIONS

Hagedorn et al., "Synthesis and Biological Properties of N-Acetyl-4-deoxy-D-neuraminic Acid" *Helvetica Chimica Acta*, vol. 69 (1986) pp. 2127-2133.

Gross et al., "N-Acetyl-4-deoxy-D-neuraminic Acid is Activated and Transferred on to Asialoglycoprotein", *Glycoconjugate*, (1984), 4:145-156.

Baumberger et al., "Synthesis of N-Acetyl-4-deoxy-neuraminic Acid", *Helvetica Chemica Acta*, vol. 69 (1986).

Baumberger et al., "4-Methylumbelliferyl 5-Acetamido-3,4,5-trideoxy-x-D-manno-2 nonulopyranosidonic Acid: Synthesis and Resistance to Bacterial Sialidases", *Helvetica Chimica Acta*, vol. 69 (1986) pp. 1927-1935.

Beau, et al., *Chemical Abstracts*, vol. 93, No. 5, Aug. 4, 1980, Columbus, Ohio, p. 394, col. 2.

Takei et al, "Enzymological Different characteristics Between Influenza A and B Virus Neuraminidases", *Biological Abstracts*, vol. 82, No. 12.

Kiyotani et al., *Biological Abstracts*, vol. 81, No. 8, Issued 1986, Abstract No. 78292.

Kiyotani et al., *Biological Abstracts*, vol. 79, No. 3, Issued 1995, Abstract No. 27461.

Liav et al., "Synthesis of 6-O-mycoloyl and 6-O-corynomycoloyl-α,α-trehalose", *Carbohydrate Research*, 125 (1984) pp. 323-328.

Kuhn et al., "Überführung Von 2-Amino-Desoxy-Hexosen in 3-Amino-3-Desoxy-Hexosen Und -Pentosen" *Bd. 636*, pp. 164-173.

Beau et al., "Synthese De L'Acide 4-O-Methyl-N-Acetylneuraminique. Partie I. Acetonation Du 3—Acetamido-3-Desoxy-D-glycero-D-galaco-Heptose Diethyldithioacetal", *Carbohydrate Research*, vol. 65 (1978) pp. 1-10.

Warner et al., "Synthesis of 2'-(4-Methylumbelliferyl)-α-D-Nacetylneuraminic Acid and Detection of Skin Fibroblas Neuraminidase in Normal Humans and in Sialidosis", *4-MU-NANA Neuraminidase*, vol. 18, No. 13, pp. 2783.

Rothermel et al. "Phase-transfer-catalyzed synthesis of aryl -ketosides of N-acetylNfuraminic acid. A 2-methylfluoran-6yl glycoside of N-acetylneuraminic acid, 2-methyl-6-(5-acetamido-3,5-dideoxy-D-galacto-nonyulopyranosylonic acid)xanthene-9-spiro-1", 1990.

"A new substrate for neuraminidase assay." Carbohydrate Research, vol. 196, pp. 29-40, 1990.

4,7-DIALKOXY N-ACETYLNEURAMINIC ACID DERIVATIVES AND METHODS FOR DETECTION OF INFLUENZA TYPE A AND B VIRUSES IN CLINICAL SPECIMENS

The present invention provides chromogenic and fluorogenic 4,7-dialkoxy-N-acetylneuraminic acid substrates which can be used to detect influenza types A and B in clinical samples or specimens. More particularly, the present invention provides 4,7-dialkoxy-N-acetylneuraminic acid substrates which can be used to distinguish between various viruses having neuraminidase reactivity. Thus, influenza type A and B viruses can be distinguished from parainfluenza type 1, 2, 3, and 4 and mumps viruses using the 4,7-dialkoxy-N-acetylneuraminic acid derivatives of this invention.

BACKGROUND OF THE INVENTION

Infectious diseases are the single most common reason for physician office visits. Viruses are responsible for more of these infections than all other groups of microorganisms combined. Of all the various infections caused by viruses, the respiratory viruses (influenza A and B; parainfluenza 1, 2, 3, and 4; respiratory syncytial virus; and adenovirus) are the most prevalent as a group. The lethality of the influenza virus was discovered in as early as 430 BC in the plague of Athens (Langmuir et al., *New Engl. J. Medicine*, 313 (1985) 1027). Influenza is the number one cause of acute respiratory illness and a contributor to the sixth leading cause of death in the United States annually (*Monthly Vital Statistics Report*, Vol.43, No. 6 (1995)). As a result, the development of diagnostic methods for viruses and viral infections has become increasingly important.

The rapid diagnosis of viral infections has also become an integral part of good medical practice. Some viruses have definable antigens against which antibodies can be produced. Therefore, immunoassays have been widely used for the measurement of the presence of a virion. Where it is desirable to measure a broader group of virions, it may be possible to detect a particular component of the virus. For example, influenza viruses express surface glycoproteins having neuraminidase (sialidase) activity. The neuraminidase enzyme hydrolyzes substrates that contain 2-ketosidically linked N-acetylneuraminic acid (Neu5Ac, also known as sialic acid). Neu5Ac consists of a backbone of nine carbon atoms, a carboxyl group and an N-acetyl group. The general structure, as well as the numbering system used to denote the carbon atoms, is shown below.

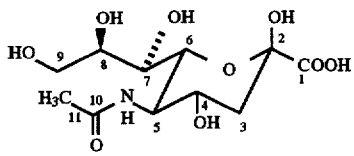

When a virion with neuraminidase activity is incubated with a chromogenic or fluorogenic glycoside of Neu5Ac, the enzyme will cleave the chromogenic or fluorogenic aglycon from the substrate, and the reaction product will indicate the presence of a virion. Throughout this specification, the N-acetyl group attached to the 5-position carbon in the above formula will be denoted as AcHN.

One method for detecting the presence of a virus through the reaction of an enzyme with a chromogenic substrate for the enzyme is described in U.S. Pat. No. 5,252,458, which is incorporated herein by reference. An assay for the direct measurement of influenza neuraminidase was developed by Yolken et al. (*J. Infectious Diseases*, 142 (1980) 516–523).

Yolken et al. used the 4-methylumbelliferyl-2-ketoside of Neu5Ac as a fluorescent substrate to measure neuraminidase activity in preparations containing small quantities of cultivated virus as well as in some nasal wash specimens from human volunteers infected with the influenza virus. Yolken et al. suggested that "successful development of fluorometric enzyme assays for the detection of influenza neuraminidase might thus provide for a practical means of influenza diagnosis that is sufficiently rapid to allow for the institution of appropriate preventive and therapeutic interventions." According to Yolken et al., colorimetric assays were insufficiently sensitive for clinical applications. In contrast, Yolken et al. noted that fluorometric assays might be suitable for detecting influenza neuraminidase in clinical samples.

Pachucki et al. (*J. Clinical Microbiology*, 26 (1988) 2664–2666) tested the 4-methylumbelliferyl-2-ketoside of Neu5Ac on clinical specimens collected from influenza patients. Due to its low sensitivity, the assay was not useful in detecting neuraminidase directly and rapidly in clinical specimens. The assay did, however, identify 91% of virus-positive isolates 25 hours after inoculation of tissue cultures.

The use of modified Neu5Ac substrates can increase the specificity of the neuraminidase assay. In sialic acids, the 4-position carbon (C-4) has been reported to play an important role in enzyme-substrate interactions. Further, since it is known that salivary bacterial enzymes exhibit neuraminidase activity (Varki et al., *J. Biol. Chem.*, 258 (1983) 12465–12471), it is essential to eliminate these undesired interactions. It has already been shown that ketosides of 4-methoxy-Neu5Ac are resistant towards certain bacterial sialidases, but are cleaved rapidly by certain viral sialidases (Beau et al., *Eur. J. Biochem.*, 106 (1980) 531–540).

Although modification of the 4-position of N-acetylneuraminic acids provides specificity between certain viral and certain bacterial neuraminidase reactivity, it would still be desirable to obtain substrates which allow further specificity or differentiation between the various viral neuraminidase reactivities while maintaining the specificity between viral and bacterial neuraminidase reactivities. Such substrates would allow, for example, high specificity for particular types of neuraminidase-containing viruses and allow better and more directed treatment regimes. Such substrates would also allow for more accurate surveillance of viral infections and more focused medical intervention as appropriate. The chromogenic and fluorogenic 4,7-modified N-acetylneuraminic acid substrates of the present invention allow for further specificity or differentiation between the various viral neuraminidase reactivities while maintaining the specificity between viral and bacterial neuraminidase reactivities.

SUMMARY OF THE INVENTION

This invention relates to chromogenic and fluorogenic 4,7-modified N-acetylneuraminic acid substrates which can be used for the detection and identification of influenza viruses in clinical specimens. More specifically, this invention relates to chromogenic and fluorogenic 4,7-dialkoxy N-acetylneuraminic acid substrates which can be used for the detection and identification of influenza viruses in clinical specimens. These 4,7-modified N-acetylneuraminic acid substrates can be used in diagnostic tests to distinguish between influenza type A and B viruses and other viruses possessing neuraminidase enzymes in clinical specimens. This invention also relates to diagnostic methods employing such substrates.

As used herein the terms "chromogenic or fluorogenic group" and "marker or reporter group" are intended to include, without limitation, molecules that exhibit absorbance or fluorescence. The term "color" is likewise intended to include, without limitation, absorbance and fluorescence.

It is an object of this invention to provide chromogenic and fluorogenic 4,7-modified N-acetylneuraminic acid substrates useful in diagnostic methods for the detection of viruses. Another object of this invention is to provide a practical, convenient, and cost effective method for the detection of influenza type A and B viruses in clinical specimens. Another object of this invention is to provide a practical, convenient, and cost effective diagnostic method which can distinguish between influenza type A and B viruses and other viruses having general neuraminidase reactivity in clinical specimens.

Still another object of this invention is to provide a 4,7-dialkoxy-N-acetylneuraminic acid of the general formula

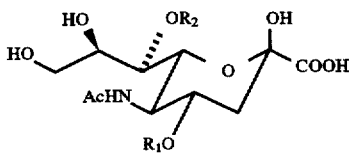

wherein $R_1$ and $R_2$ are alkyl groups containing 1 to 4 carbon atoms. Preferably, both $R_1$ and $R_2$ are methyl groups.

Still another object of this invention is to provide a 4,7-dialkoxy-N-acetylneuraminic acid substrate of the general formula

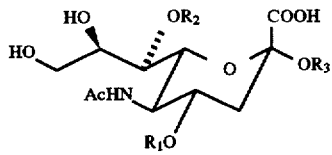

wherein $R_1$ and $R_2$ are alkyl groups containing 1 to 4 carbon atoms and $R_3$ is a chromogenic or fluorogenic group. Preferably, both $R_1$ and $R_2$ are methyl groups and $R_3$ is a chromogenic group.

Still another object of this invention is to provide a method for detecting influenza type A and B viruses in a clinical sample from an individual suspected of having a respiratory viral infection, said method comprising:

(1) incubating the clinical sample with a chromogenic or fluorogenic 4,7-dialkoxy N-acetylneuraminic acid substrate of the general formula

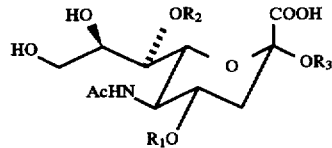

wherein $R_1$ and $R_2$ are alkyl radicals containing 1 to 4 carbon atoms and $R_3$ is a chromogenic or fluorogenic group that exhibits a distinct and characteristic color when cleaved from the substrate or a salt of the substrate;

(2) observing the incubated clinical sample to determine whether the distinct and characteristic color is formed, wherein the formation of the distinct and characteristic color indicates the presence of influenza type A or B viruses in the clinical sample.

Still another object of this invention is to provide a method for detecting influenza type A and B viruses in a clinical sample from an individual suspected of having a respiratory viral infection, said method comprising:

(1) dividing the clinical sample into a first portion and a second portion;

(2) incubating the first portion with a chromogenic or fluorogenic 4,7-dialkoxy N-acetylneuraminic acid first substrate of the general formula

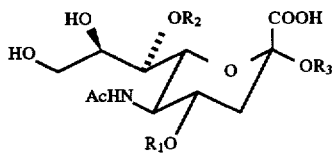

wherein $R_1$ and $R_2$ are alkyl radicals containing 1 to 4 carbon atoms and $R_3$ is a first chromogenic or fluorogenic group that exhibits a distinct and characteristic first color when cleaved from the first substrate or a salt of the first substrate;

(3) observing the incubated first portion to determine whether the distinct and characteristic first color is formed, wherein the formation of the distinct and characteristic first color indicates the presence of influenza type A or B viruses in the clinical sample;

(4) incubating the second portion with a chromogenic or fluorogenic 4-alkoxy N-acetylneuraminic acid second substrate of the general formula

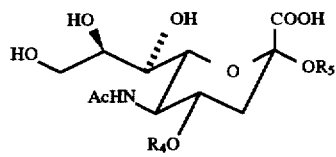

wherein $R_4$ is an alkyl radical containing 1 to 4 carbon atoms and $R_5$ is a second chromogenic or fluorogenic group that exhibits a distinct and characteristic second color when cleaved from the second substrate or a salt of the second substrate; and (5) observing the incubated second portion to determine whether the distinct and characteristic second color is formed, wherein the formation of the distinct and characteristic second color indicates the presence of neuraminidase reactive viruses in the clinical sample;

wherein the presence of the first and second colors indicates the presence of influenza type A or B viruses alone or in combination with neuraminidase reactive viruses other than influenza type A and B viruses in the clinical sample;

wherein the presence of the second color and the absence of the first color indicates neuraminidase reactive viruses other than influenza type A and B viruses in the clinical sample; and wherein the absence of the first and second colors indicates the absence of neuraminidase reactive viruses in the clinical sample.

Other objects, advantages, features, and characteristics of the present invention will become more apparent upon consideration of the following description and the appended claims.

DETAILED DESCRIPTION OF THE INVENTION

The present invention relates to a 4,7-dialkoxy-N-acetylneuraminic acid of the general formula

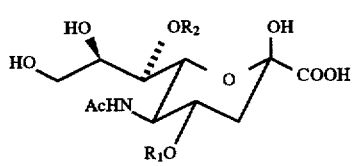

wherein $R_1$ and $R_2$ are alkyl groups containing 1 to 4 carbon atoms. $R_1$ and $R_2$ may be the same or different alkyl groups. The higher alkyl groups (i.e., when R contains 3 to 4 carbon atoms) can include linear and branched isomers. Preferably $R_1$ and $R_2$ are alkyl groups containing 1 or 2 carbons atoms; more preferably $R_1$ and $R_2$ are both methyl groups.

The 4,7-dialkoxy-N-acetylneuraminic acid of the present invention can be prepared using the following general reaction scheme:

The starting material 1 (8,9-O-isopropylidine-methyl estermethyl ketoside derivative of Neu5Ac) is prepared from Neu5Ac as generally described in our U.S. Pat. No. 5,556,963 issued Sep. 17, 1996 (application Ser. No. 08/286,573 filed Aug. 5, 1994), which is hereby incorporated by reference. Neu5Ac is commercially available (MediHerb Inc., 4540 S. Navajo #1, Englewood, Colo. 80110). It may also be synthesized enzymatically from N-acetyl-D-mannosamine and pyruvic acid using the procedure described by Kim et al., *J. Am. Chem. Soc.*, 110 (1988) 6481, and illustrated by the following equation:

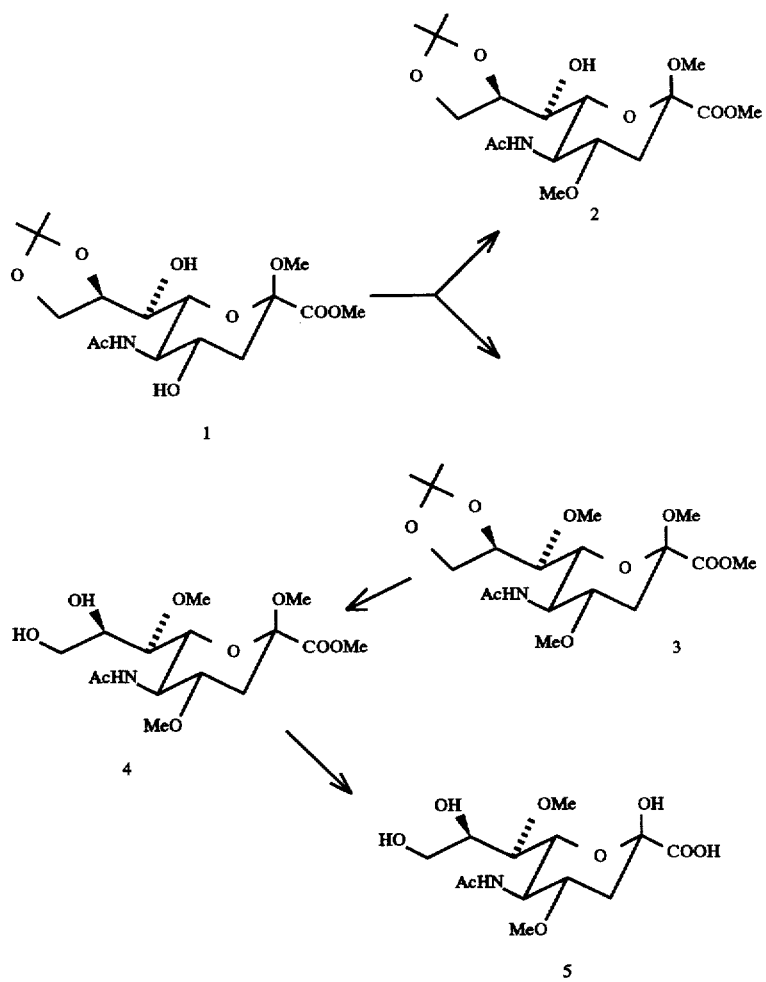

Scheme 1

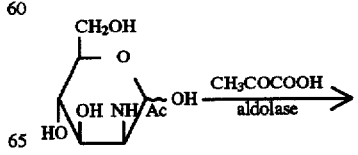

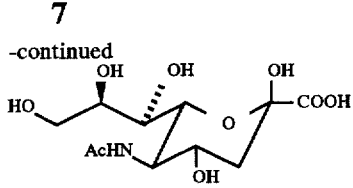

The enzymatic reaction can be monitored by thin layer chromatography (TLC) and the product can be purified by ion exchange chromatography.

Neu5Ac is first converted into an alkyl ester alkyl ketoside of general formula

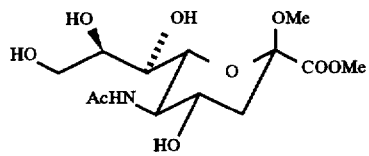

as described in U.S. Pat. No. 5,556,963. The vicinal hydroxyl groups at C-8 and C-9 of this methyl ester methyl ketoside are protected by the formation of a ketal (1) by treatment with effective amounts of acetone and an acid catalyst to form the ketal. Suitable acid catalysts include p-toluenesulfonic acid, salts of p-toluenesulfonic acid such as the pyridinium salt (PPTS) and other salts, $ZnCl_2$, $FeCl_3$, and the like. The preferred acid catalyst is the non-hygroscopic pyridinium salt of p-toluenesulfonic acid.

The protected methyl ester methyl ketoside (1) is then alkylated to form a mixture of compound 2 containing an alkoxy group at the 4-position and compound 3 with alkoxy groups at both the 4- and 7-positions. Alkylation of the hydroxyl group at C-4 and C-7 may be methylation, ethylation, propylation, or butylation, whereby the hydroxy group at C-4 in 2 is converted to a —OR group and the hydroxy groups at C-4 and C-7 in 3 are converted to —OR groups where R is an alkyl radical containing 1 to 4 carbon atoms. Preferably, the alkylation at C-4 and/or C-7 is methylation or ethylation, whereby 4-methoxy or 4-ethoxy derivatives or 4,7-dimethoxy or 4,7-diethoxy derivatives are obtained. More preferably, the alkylation at C-4 and/or C-7 is methylation, whereby 4-methoxy or 4,7-dimethoxy derivatives are obtained. Introduction of higher alkyl groups at the C-4 and C-7 positions is generally slower than methylation and the yields are somewhat lower. Furthermore, chromogenic substrates with higher alkyl groups tend to be less susceptible to enzymatic cleavage than 4,7-dimethoxy-Neu5Ac, thereby resulting in less sensitive assays. Nonetheless, for some specific applications and assays, such higher alkyl groups at C-4 and C-7 may be useful and even preferred.

Alkylation at the more sterically hindered free hydroxyl group at C-7 can be encouraged by controlling the reaction conditions as described immediately hereafter. In accordance with the process, intermediate 1 is treated with an excess (generally greater than about 1.5 molar equivalents) of an alkylating agent in about an 80% dispersion of sodium hydride. The alkylating agent is selected from the group consisting of dimethyl sulfate, diethyl sulfate, dipropyl sulfates, and dibutyl sulfates. The reaction is generally conducted at a temperature of from about 0° C. to about 30° C. for about 10 minutes to about 48 hours. Preferably the reaction temperature is in the range of about 0° C. to about 22° C. Longer reaction times are generally preferred when forming the higher alkoxy groups at the 4- and 7-positions. In a preferred embodiment of the invention, a methylation reaction to form methoxy groups at C-4 and C-7 is conducted at a temperature of from about 0° C. to about 30° C., more preferably from about 0° C. to about 22° C., for about 10 minutes to about 30 minutes. In another preferred embodiment of the invention, an ethylation reaction to form ethoxy groups at C-4 and C-7 is conducted at a temperature of from about 0° C. to about 30° C., more preferably from about 0° C. to about 22° C., for about 1 hour to about 24 hours.

Treatment of the protected methyl ester methyl ketoside 1 with excess alkylating agent (e.g., dimethyl sulfate) produces a mixture of compound 2 containing an alkoxy group at the 4-position and compound 3 with alkoxy groups at both the 4- and 7-positions. Generally, an excess of about 1.5 molar equivalents of alkylating agent is used. Preferably about 1.5 to about 2.0 molar equivalents of alkylating agent is used. Generally the amount of the desired compound 3 is increased relative to compound 2 as the amount of alkylation agent increases. The reaction mixture resulting from such treatment generally contains the 4-alkoxy compound 2 as the major product and about 10 to 20 weight percent of the 4,7-dialkoxy compound 3. Partial separation of the compounds 2 and 3 can be obtained, for example, by column chromatography and subsequent crystallization from an acetone-hexane mixture which preferentially removes the 4-alkoxy compound 2. The resulting residue contains a mixture of the two compounds enriched with the 4,7-dialkoxy material; generally the molar ratio of the two compounds is increased to at least about 1:1.

Removal of the ketal group from compound 3 is achieved by treatment with about 80% acetic acid. Acetic acid hydrolysis can also result in partial acetylation at the C-9 hydroxyl group. Hence, the hydrolysis product can be treated with sodium methoxide to remove any acetate groups on C-9. Final deprotection of 4 is performed by alkaline treatment and subsequent acid hydrolysis to give the final 4,7-dialkoxy-Neu5Ac product (5). Of course, the 4-alkoxy compound 2 present in the mixture will also be treated in a similar manner to yield the corresponding 4-alkoxy-Neu5Ac compound.

The resulting 4,7-dialkoxy-Neu5Ac can be further utilized through coupling to any suitable marker or reporter group, including for example, a chromogenic or fluorogenic marker group. The preferred marker or reporter group is a chromogenic group, including, for example, 4-chloro-1-naphthol, 6-bromo-1-naphthol, and 5-bromo-4-chloro-indole. Chromogenic modified 4,7-dialkoxy-Neu5Ac can be incorporated into a neuraminidase assay useful for detecting viral neuraminidase activity from influenza type A and B in clinical samples or specimens. Methods for synthesizing and using such 4,7-position modified chromogenic N-acetylneuraminic acid substrates in viral assays are similar to those described for the related 4-position modified substrates in PCT Publication Number WO 91/09972; Yolken et al., *J. Infectious Diseases*, 142 (1980) 516–523; and Pachucki et al., *J. Clinical Microbiology*, 26 (1988) 2664–2666, each of which are incorporated herein by reference. Of course, the present 4,7-dialkoxy-N-acetylneuraminic acids can be used to form other chromogenic- and fluorogenic-containing derivatives and can be used in other viral assays.

Generally the chromogenic or fluorogenic marker group can be incorporated into the 4,7-dialkoxy-Neu5Ac (5) using the following reaction scheme (using 5-bromo-3-indolyl as an example marker group):

Scheme 2

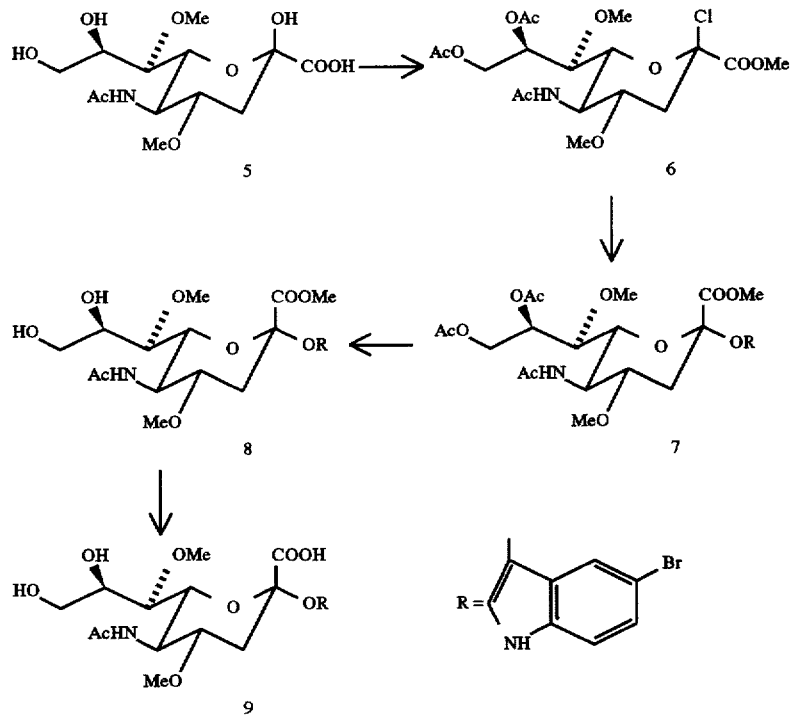

Compound 5 is first converted into the corresponding methyl ester derivative by treatment with concentrated trifluoroacetic acid and methanol, and the ester is then reacted with excess acetyl chloride to form the chloroacetate-methyl ester derivative of 4,7-dialkoxy-Neu5Ac (6). Coupling of 6 with the sodium salt of 5-bromo-3-indolyl gives rise to the 5-bromo-indol-3-ol-4,7-dimethoxy-N-acetylneuraminic acid-acetoxy-methyl ester (7). De-acetylation of 7 is effected by treatment with sodium methoxide in methanol to yield compound 8 and subsequent treatment with sodium hydroxide gives the sodium salt of 5-bromo-3-indolyl-4,7-dimethoxy-N-acetylneuraminic acid (9). Of course, the 4-alkoxy-Neu5Ac in the mixture undergoes similar coupling reactions to form the 5-bromo-3-indolyl-4-methoxy-N-acetylneuraminic acid salt.

The coupled 4,7-dialkoxy derivative 9 is then separated from the mixture of the two coupled compounds (i.e., the 4-alkoxy and 4,7-dialkoxy derivatives) by high performance liquid chromatography (HPLC) using, for example, a C18 reverse-plate silica column. The mixture of the coupled products can be dissolved in water and loaded onto the column. The products are separated by an increasing gradient of methanol with the appropriate fractions collected and pooled. The resulting purified 5-bromo-3-indolyl-4,7-dimethoxy-N-acetylneuraminic acid (9) can be dried and stored until use. Generally, the resulting product is essentially free of the 4-methoxy derivative. It is important that this mixture be essentially free of the 4-methoxy derivative since it is highly reactive with mumps virus and other neuraminidase-containing viruses.

As noted above, the chromogenic or fluorogenic 4,7-dialkoxy derivatives of this invention are of the general formula

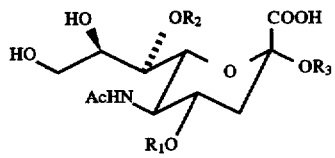

wherein $R_1$ and $R_2$ are alkyl groups containing 1 to 4 carbon atoms and $R_3$ is a chromogenic or fluorogenic group. $R_1$ and $R_2$ may be the same or different alkyl groups. Preferably, both $R_1$ and $R_2$ are methyl groups and $R_3$ is a chromogenic group. More preferably, $R_3$ is 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, or 6-bromo-2-naphthyl. Even more preferably, $R_3$ is 4-methylumbelliferyl, 5-bromo-4-chloro-3-indolyl, or 5-bromo-3-indolyl. The most preferred $R_3$ is 5-bromo-3-indolyl. Simple salts of these substrates, such as the $Na^+$, $K^+$, and $NH_4^+$ salts, may also be used.

Examples of 4,7-dialkoxy chromogenic Neu5Ac derivatives falling within the above formula include 4-methylumbelliferyl-4,7-dimethoxy-N-acetylneuraminic acid-alpha-ketoside, 2-nitrophenyl-4,7-dimethoxy-N-acetylneuraminic acid-alpha-ketoside, 4-nitrophenyl-4,7-methoxy-N-acetylneuraminic acid-alpha-ketoside, 3-cyanoumbelliferyl-4,7-dimethoxy-N-acetylneuraminic acid-alpha-ketoside, 3-resorufin-4,7-dimethoxy-N-acetylneuraminic acid-alpha-ketoside, 5-bromo-4-chloro-3-indolyl-4,7-dimethoxy-N-acetylneuraminic acid-alpha-ketoside, 5-bromo-3-indolyl-4,7-dimethoxy-N-acetylneuraminic acid-alpha-ketoside, 3-indolyl-4,7-dimethoxy-N-acetylneuraminic acid-alpha-ketoside, 2-[4-

(4-nitrophenylazo)phenyl]-4,7-dimethoxy-N-acetyl-neuraminic acid-alpha-ketoside, 2-[4-(4-nitrophenylazo) resorcinyl]-4,7-dimethoxy-N-acetylneuraminic acid-alpha-ketoside, 3-methoxyphenyl-4,7-dimethoxy-N-acetyl-neuraminic acid-alpha-ketoside, 3-dimethylaminophenyl-4, 7-dimethoxy-N-acetylneuraminic acid-alpha-ketoside, 6-bromo-2-naphthyl-4,7-dimethoxy-N-acetylneuraminic acid-alpha-ketoside, 4-chloro-1-naphthyl-4,7-dimethoxy-N-acetylneuraminic acid-alpha-ketoside, as well as the corresponding 4,7-diethoxy, 4,7-dipropyl, and 4,7-dibutyl derivatives. Generally, the 4,7-dimethoxy derivatives are preferred. If desired, "mixed" 4,7-dialkoxy derivatives (e.g., 4-methoxy-7-ethoxy) can be used.

The chromogenic or fluorogenic 4,7-dialkoxy derivatives can be used in diagnostic tests for influenza type A and B viruses in clinical samples. The clinical samples that are tested in the invention will typically be pharyngeal, nasopharyngeal, or respiratory secretions collected from patients suffering, or suspected of suffering, from influenza as wash, swab, or expectorate specimens. The wash, expectorate, or swab will preferably be combined with an aqueous buffer solution containing a stabilizer prior to mixing with the substrate. The buffer solution generally contains a buffer that maintains the pH at about 4 to 7, preferably 5.5 to 6.5, optionally about 0.1% to 10% by weight nonionic detergent, a small amount (1–20 mM) of alkaline earth metal cation (Ca, Mg, preferably Ca), and a sufficient amount of a stabilizer selected from the group consisting of alditols, monosaccharides, and disaccharides to enhance the thermal stability of the neuraminic acid in the sample.

The volume of buffer solution combined with the specimen will normally be 0.1 to 2 ml. The buffer may be organic or inorganic. Suitable buffers include, for example, conventional buffers of organic acids and salts thereof such as citrate buffers (e.g., monosodium citrate-disodium citrate mixture, citric acid-trisodium citrate mixture, citric acid-monosodium citrate mixture, etc.), acetate buffers (e.g., acetic acid-sodium acetate mixture), succinate buffers (e.g., succinic acid-monosodium succinate mixture, succinic acid-sodium hydroxide mixture, succinic acid-disodium succinate mixture, etc.), tartrate buffers (e.g., tartaric acid-tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumerate mixture, monosodium fumarate acid-disodium fumerate mixture), gluconate buffers (e.g., gluconic acid-sodium gluconate mixture, gluconic acid-sodium hydroxide mixture, gluconic acid-potassium gluconate mixture, etc.) oxalate buffers (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate-mixture, etc.), acetate buffers (e.g., acetic acid-sodium acetate mixture, acetic acid-sodium hydroxide mixture, etc.), malate buffers (e.g., D,L-malic acid-disodium malate mixture), phosphate buffers (e.g., monosodium phosphate-disodium phosphate mixture, monosodium phosphate-sodium hydroxide mixture, trisodium phosphate-hydrochloric acid mixture, etc.), 2-(N-morpholino) ethanesulfonic acid, [bis-(2-hydroxyethyl)imino]tris(hydroxymethyl)methane, N-2-acetamidoiminodiacetic acid, 1,3-bis[tris(hydroxymethyl) methylamino]propane, piperazine-N,N'-2-ethanesulfonic acid), N-2-acetamido-2-aminoethanesulfonic acid, 3-(N-morpholino)-2-hydroxypropanesulfonic acid, 3-(N-morpholino)propanesulfonic acid, 2-[tris(hydroxy-methyl) methylamino]ethanesulfonic acid, N-2-hydroxyethylpiperazine-NN'-2-ethanesulfonic acid, 3-[tris-(hydroxymethyl)methylamino]-2-hydroxypropanesulfonic acid.

Non-ionic detergents useful in the buffer solution include, for example, the Pluronics, such as Polysorbate 20 or Polysorbate 80, Triton X-100, NP-40, and alkyl glucosides such as $C_8$ and $C_9$ alkyl glucosides. The detergent is an optional component and facilitates release of the neuraminidase from the viral envelope. Stabilizers that are used in the buffer solution include, for example, trihydric or higher alditols, such as glycerin, erythritol, arabitol, xylitol, sorbitol, mannitol, the hexoses glucose and fructose and the disaccharide sucrose. These stabilizers can be used alone or in combination. In order to stabilize the activity of the neuraminidase-containing viruses, the stabilizers are added to the liquid formulation/excipient system in an amount from 0.2M to 2.1M and preferably, 0.6M to 2.0M. Once mixed with the buffer solution, the sample may be stored for prolonged periods, preferably at 2° C. to 8° C., without significant loss of neuraminidase activity.

The substrate will normally be added to the buffered, stabilized sample in amounts ranging between 0.05 mM and 0.5 mM. The mixture is incubated at ambient temperature to physiological temperature (i.e., about 18° C. to 40° C.) for a time sufficient to permit any neuraminidase in the sample to react with the substrate. That time will normally be in the range of 1 minute to 4 hours, usually at 5 to 120 minutes, and more usually 30 to 60 minutes. If there is neuraminidase activity in the sample, the marker or reporter group will be released from the substrate and the liberated marker or reporter precipitate will impart a characteristic color to the mixture. Especially for colorimetric derivatives, the resulting reaction mixture is preferably transferred to a collection device containing a porous membrane filter and an absorbent pad to wick away the solution. Once such collection device is shown in our copending application Ser. No. 08/479,789 (filed Jun. 7, 1995), which is hereby incorporated by reference. In the presence of influenza type A and B neuraminidase, the reporter group on the 4,7-modified Neu5Ac is released by the action of neuraminidase and the resulting reporter molecule is collected as a colored precipitate on the porous filter membrane. The presence of such a colored product indicates a positive diagnosis for influenza types A and B; the absence of such a colored product indicates a negative diagnosis for influenza types A and B. Concentration or collection of the colored precipitate increases the sensitivity of the diagnostic test. Such collection devices are not, however, necessary for the practice of the invention.

The following table indicates the characteristic color generated when neuraminidase reacts with various chromogenic or fluorogenic 4,7-modified Neu5Ac derivatives and releases the reporter molecule.

| Released Reporter Molecule | Type of Detection | Color |
|---|---|---|
| 5-bromo-4-chloro-3-indolol | colorimetric/ visual | blue/purple in the presence of nitroblue tetrazolium |
| 5-bromo-3-indolol | colorimetric/ visual | blue/purple in the presence of nitroblue tetrazolium |
| 3-indolol | colorimetric/ visual | blue/purple in the presence of nitroblue tetrazolium |

| Released Reporter Molecule | Type of Detection | Color |
| --- | --- | --- |
| 4-methylumbelli-ferone | fluorometric | fluorescent emission at 454 nm after excitation at 360 nm |
| 3-cyanoumbelli-ferone | fluorometric | fluorescent emission at 454 nm after excitation at 415 nm |
| resorufin | colorimetric/visual | pink/red |
| 2-nitrophenol | colorimetric/visual | yellow |
| 4-nitrophenol | colorimetric/visual | yellow |
| nitrophenyl-azophenol | colorimetric/visual | orange |
| nitrophenyl azoresorcinol | colorimetric/visual | green blue (presence of $Mg^{++}$) |
| 3-methoxyphenol | colorimetric/visual | red to blue after reaction with diazonium salt |
| 3-dimethylamino-phenol | colorimetric/visual | red to blue after reaction with diazonium salt |
| 4-chloro-1-naphthol | colorimetric/visual | red to blue after reaction with diazonium salt |
| 6-bromo-2-naphthol | colorimetric/visual | red to blue after reaction with diazonium salt |

The present chromogenic and fluorogenic 4,7-dialkoxy Neu5Ac derivatives only exhibit the characteristic color in the presence of influenza type A and B virus. They do not exhibit the characteristic color (i.e., no release of the reporter molecule occurs) in the presence of parainfluenza types 1, 2, 3, and 4, mumps, respiratory syncytial viruses, and/or adenoviruses. Moreover, the chromogenic and fluorogenic 4,7-dialkoxy Neu5Ac derivatives do not exhibit bacterial neuraminidase reactivity. To maintain the desired degree of selectivity, the 4,7-dialkoxy Neu5Ac derivatives should be essentially free of the corresponding 4-alkoxy Neu5Ac derivatives. The maximum levels of the 4-alkoxy Neu5Ac derivatives which allow acceptable selectivity can be determined experimentally using known strains of the various types of viruses. Generally, the levels of 4-alkoxy Neu5Ac derivatives should be less than about 5 weight percent, and preferably less than about 0.5 weight percent.

A potentially more informative diagnostic test can be obtained by combining the neuraminidase reactivity and selectivity of the present chromogenic and fluorogenic 4,7-dialkoxy Neu5Ac derivatives and the chromogenic and fluorogenic 4-alkoxy Neu5Ac derivatives in a single test. In such a system, the clinical sample is divided into two portions which are then incubated separately with the 4,7-dialkoxy and the 4-alkoxy Neu5Ac derivatives, respectively. The presence and/or absence of characteristic color in the two incubated samples can be used to more closely determine the type of virus, if any, present in the clinical sample. If only influenza type A or B viruses are present in the clinical sample, then both the 4-alkoxy and the 4,7-dialkoxy derivatives will exhibit their characteristic colors of their reporter molecules. If both influenza type A or B viruses and neuraminidase reactive viruses other than influenza type A and B viruses are present in the clinical sample, then each portion will exhibit the characteristic color of its reporter molecule. If only neuraminidase reactive viruses other than influenza type A and B viruses are present in the clinical sample, then only the 4-alkoxy derivative will exhibit the characteristic color of its reporter molecule. If no neuraminidase reactive viruses are present in the clinical sample, then neither portion will exhibit the characteristic color of its reporter molecule.

Accordingly, the present invention provides simple and rapid techniques for selectively diagnosing influenza —especially types A and B—that may be carried out in the clinic or physician's office and enable the physician to prescribe the appropriate therapy to treat the infection and/or the appropriate prophylactic treatment to persons in close contact with the infected patient.

The following examples are intended to illustrate the invention.

EXAMPLE 1

The synthesis of 4,7-dimethoxy-Neu5Ac was carried out using the reactions shown in Scheme 1. A cold (ice bath temperature) solution of the isopropylidene derivative 1 (1.2 g) in about 10 ml of dry acetonitrile was saturated with nitrogen. Sodium hydride (270 mg; 80% dispersion in oil) was added and the mixture stirred for 20 minutes. Dimethyl sulfate (1 ml) was added and the stirring continued for an additional 30 minutes using an ice bath to cool the mixture. The resulting mixture was filtered through celite and the precipitate was washed with dry acetonitrile. The filtrate was evaporated and the residue was dried and extracted with acetone. After filtration, the filtrate was again evaporated. The resulting residue was dried and chromatographed on silica gel. Elution with methylene chloride/methanol (25:1) removed several byproducts. Continued elution with the same solvent system provided a syrup containing 2 and 3 which was crystallized from acetone-hexane. Crystalline 2 (177 mg) was collected. The filtrate contained a mixture of 2 and 3 (about 1:1) but with a higher proportion of 3 than the original mixture.

The filtrate containing 3 (1.22 g) was treated with 80% aqueous acetic acid (15 ml) at 85° C. for one hour. The mixture was evaporated and co-evaporated with water. The residue was chromatographed. Elution with methylene chloride/methanol (5:1) removed a minor byproduct. Continued elution with the same solvent system gave the partially deprotected product 4 (0.87 g; 80% yield).

The 4,7-dimethoxy-methyl ester methyl ketoside (4) (0.87 g) was treated with 1M sodium hydroxide (3 ml) in methanol (5 ml) and water (5 ml) at room temperature for one hour. The mixture was neutralized with Dowex 50 ($H^+$) resin; the resin was removed by filtration and washed with methanol. The combined filtrate was evaporated. The residue was treated with Dowex 50 ($H^+$) resin (1.5 g) in 0.025M hydrochloric acid at 100° C. for two hours. The resin was removed by filtration and the filtrate collected and evaporated. The residue was dried under vacuum to give essentially pure 4,7-dimethoxy-Neu5Ac (5) (0.71 g; 88% yield).

EXAMPLE 2

The synthesis of 5-bromo-3-indolyl-4,7-dimethoxy-Neu5Ac was carried out using the reactions shown in Scheme 2. Compound 5 (1.0 g) was treated with trifluoroacetic acid (0.2 ml) in methanol (25 ml) overnight at room temperature. The mixture was evaporated. The residue was dried and treated with acetyl chloride (5 ml) in methylene chloride (5 ml). The reaction mixture was stirred overnight at room temperature and then evaporated. The residue was dried to provide the crude chloride 6 (1.36 g). The crude product 6 was not further purified because of its instability.

A suspension of the crude product 6 (0.7 g) and 1-acetyl-5-bromo-indol-3-ol (0.26 g) in acetone (5 ml) was saturated with nitrogen. A 1M sodium hydroxide solution (1 ml) was added. The reaction mixture was stirred under nitrogen for one hour. After evaporation, the residue was dried and chromatographed on silica gel. Elution with methylene chloride/methanol (25:1) removed the unreacted chromogen (0.128 g). Continued elution with the same solvent system gave fractions containing mainly the coupled product 7 (0.114 g). The coupled product 7 (0.114 g) was treated with 1M sodium methoxide in methanol (0.1 ml) for 30 minutes at room temperature. After neutralization with Dowex 50 ($H^+$) resin, the resin was removed and washed with methanol. The combined filtrate was evaporated. The residue was dried and chromatographed on silica gel. Fractions containing mainly the coupled product 8 were pooled and evaporated to give about 60 mg of 8.

The coupled product 8 (60 mg) was treated with 1M sodium hydroxide (0.5 ml) in 50% aqueous methanol (5 ml) for 30 minutes at room temperature. The mixture was neutralized with Dowex 50 ($H^+$) resin. The resin was removed by filtration and washed with methanol. The combined filtrate was evaporated and the residue was purified by HPLC. The first fractions contained an uncoupled product. The coupled material appeared as a broad peak which consisted of both coupled 4-methoxy-Neu5Ac and coupled 4,7-dimethoxy-Neu5Ac product 9. Since a minor amount of the coupled 4-methoxy derivative could render the diagnostic analysis unspecific, only highly pure fractions containing 9 were pooled. Upon evaporation, highly purified 9 (4 mg) was collected; the collected material contained less than about 5 weight percent of the corresponding 4-alkoxy derivative.

EXAMPLE 3

This example demonstrates the specificity of the 5-bromo-3-indolyl-4,7-dimethoxy-Neu5Ac (9) of Example 2 in diagnostic tests for influenza A and B in cultured viruses. Viruses were grown from fresh patient isolates or frozen stock cultures using the appropriate cell line, medium, and incubation conditions suitable for the growth and culture of the particular virus. The following cells were used: (1) RMK (Rhesus monkey kidney) cells for influenza and parainfluenza viruses; (2) HEp-2 (human larynx carcinoma) cells for respiratory syncytial virus and adenovirus; and (3) VERO (African Green monkey kidney) cells for mumps. All cells were grown to near-confluent monolayers in tubes or flasks with minimum essential medium with 5–10 percent serum at 37° C. Virus infections were carried out in the appropriate cell lines with minimum essential medium without serum at 37° C.

Virus-infected cultures were monitored and confirmed by observing the appearance of characteristic cytopathic effects and by testing with immunofluorescence assays using virus-type specific monoclonal antibodies. The following characteristic cytopathic effects were observed for each of the viruses used as follows: (1) Influenza A and B: areas of large, irregularly shaped, granular, or vaculated cells with progressive degeneration of the cell monolayer; (2) Parainfluenza 1: small rounded cells throughout the cell monolayer; (3) Parainfluenza 2: dark, granular, and irregular syncytia which retract from the cell monolayer; (4) Parainfluenza 3: elongated, fusiform cells that eventually retract and pull away from the cell monolayer; (5) Respiratory syncytial virus: large, irregularly shaped syncytia that appear as large multinucleated cells with indistinct borders throughout the cell monolayer; (6) Adenovirus: large, rounded pycnotic cells which eventually aggregate into rounded cell sheets and detach from the culture vessel; and (7) Mumps: syncytia with vacuolation and cell degeneration throughout the cell monolayer. Commercial virus type-specific monoclonal antibodies were used in fluorescence assays to confirm growth of each virus in the inoculated cultures. Cells from the infected cultures were methanol fixed on glass slides or coverslips and then incubated at 37° C. with fluorescein-labeled monoclonal antibodies. Both direct and indirect fluorescence assays were used. For the direct assays, the fixed, virus infected cells were incubated for 30 minutes with virus type-specific, fluorescein isothiocyanate (FITC) labeled monoclonal antibodies. For the indirect assays, the fixed, virus infected cells were incubated for 30 minutes with virus type-specific, unlabeled monoclonal antibodies, followed by incubation for an additional 30 minutes with secondary FITC-labeled monoclonal antibodies. The slides or coverslips were overlaid with mounting medium and examined using a fluorescent microscope. A positive virus result was verified by the presence of a characteristic, virus-specific, apple-green staining. The presence of progressive and characteristic cytopathic effects (along with accompanying specific virus confirmation with fluorescence assay) was an indication that the particular inoculated virus had proliferated maximally.

After achieving maximal virus growth and confirmation of the presence of the appropriate virus, the culture fluids were harvested for evaluation with the 4-methoxy-N-acetylneuraminic acid and 4,7-dimethoxy-N-acetylneuraminic acid chromogenic substrates. Virus-containing culture fluids (0.1 ml) were mixed with the chromogenic substrates in a 1 or 2 ml solution containing excipents and buffer designed to achieve optimal pH and neuraminidase activity. The buffer/excipient solution contained 35 mM malic/malate buffer with 10 mM calcium chloride, 0.85 percent sodium chloride, 0.1 percent mannitol, 0.5 percent methanol, and 0.1 percent methyl paraben. The substrate and buffer combination at a pH of about 5.4 was determined to provide specific detection of neuraminidase-producing viruses with clearly negative results for non-neuraminidase-producing viruses and virus-negative cultures.

The test solutions were incubated at 37° C. for about one hour after which the reaction was stopped by the addition of 0.2 ml of a buffer concentrate which changed the pH to about 9 and helped increase the precipitation of the released chromogen. The completed reaction mixture was then transferred to a collection device containing a selectively porous membrane filter and an absorbent pad to wick away the solution whereby the precipitate is concentrated. The collection device is described in our copending application Ser. No. 08/479,789 (filed Jun. 7, 1995). The appearance of an appropriately colored precipitate indicated a positive reaction whereas the absence of such an appropriately colored precipitate indicated a negative reaction. Using the 5-bromo-3-indolyl chromogen, the characteristic color of the precipitate for a positive test was blue.

The following viruses were used to test the 5-bromo-3-indolyl-4-methoxy-N-acetylneuraminic acid substrate (BI-4-MeONeu5Ac) and the 5-bromo-3-indolyl-4,7-dimethoxy-N-acetylneuraminic acid substrate (BI-4,7-(MeO)$_2$Neu5Ac).

| Virus | Titer | Source |
| --- | --- | --- |
| Influenza A | #1 | ATCC #VR97 Strain A1/FM/1/47 |
|  | #2 | ATCC #VR97 Strain A1/FM/1/47 |
| Influenza B | #1 | University of New Mexico Clinical Isolate #92-7471 |
|  | #2 | University of New Mexico |

-continued

| Virus | Titer | Source |
|---|---|---|
| | | Clinical Isolate #92-7471 |
| Parainfluenza Type 1 | #1 | Cardinal Glennon Children's Clinical Isolate #92-48 |
| | #2 | Cardinal Glennon Children's Clinical Isolate #92-7902 |
| Parainfluenza Type 2 | #1 | University of New Mexico Clinical Isolate #92-6173 |
| | #2 | University of New Mexico Clinical Isolate #92-6173 |
| Parainfluenza Type 3 | #1 | Cardinal Glennon Children's Clinical Isolate #94-5576 |
| | #2 | University of New Mexico Clinical Isolate #93-4546 |
| Mumps | #1 | ATCC #VR-106 Strain Enders |
| | #2 | ATCC #VR-106 Strain Enders |
| | #3 | ATCC #VR-106 Strain Enders |
| Respiratory Syncytial | #1 | ATCC #VR-26 Strain Long |
| Adenovirus | #1 | University of New Mexico Clinical Isolate #93-0539 |

The following results were obtained using these various virus cultures. The virus cultures were grown to their maximal titers (as determined by observance of extensive—about 90 to 100 percent—virus-characteristic cytopathic effects in the cell sheet and confirmation with fluorescence assays of bright apple-green, virus-specific staining in the majority of cells) to insure that any reaction differences were not due to undetectable viral concentrations.

| Virus | Titer | BI-4-MeONeu5Ac | BI-4,7-$(MeO)_2$Neu5Ac |
|---|---|---|---|
| Influenza A | #1 | 1+ | 1+ |
| | #2 | 1+/2+ | 2+ |
| Influenza B | #1 | 1+ | 1+ |
| | #2 | 3+ | 3+ |
| Para-influenza Type 1 | #1 | negative | negative |
| | #2 | 2+ | negative |
| Para-influenza Type 2 | #1 | negative | negative |
| | #2 | 1+/2+ | negative |
| Para-influenza Type 3 | #1 | indeter-minate | negative |
| | #2 | negative | negative |
| Mumps | #1 | negative | negative |
| | #2 | 1+ | negative |
| | #3 | 3+ | negative |
| Respiratory Syncytial | #1 | negative | negative |
| Adenovirus | #1 | negative | negative |

A rating scale of 1+ to 3+, based on the intensity of the reaction color, was used to indicate relative levels of detectable neuraminidase activity. The rating colors were matched to color samples from a standard reference source (The Pantone® Color Specific Book 747XR). A rating of 1+ (light color) indicates a low positive, 2+ (moderate color) indicates a moderate positive, and 3+ (deep color) indicates a high positive. A negative result is indicated by the absence of the characteristic color. An indeterminate result is indicated if a very faint trace or suggestion of the characteristic color may be present by visual observation.

As can be seen from these results, viruses containing influenza type A and B neuraminidase were the only tested organisms which gave a positive reaction with both the 4-methoxy-Neu5Ac and the 4,7-dimethoxy-Neu5Ac substrates undiluted and at all dilutions tested. For parainfluenza types 1, 2, and 3 and the mumps virus, the 4-methoxy-Neu5Ac substrate gave both negative and positive reactions depending on the dilution. The 4,7-dimethoxy-Neu5Ac substrate gave a negative reaction with parainfluenza types 1, 2, and 3 and the mumps virus undiluted and at all dilutions. Non-neuraminidase containing viruses (i.e., respiratory syncytial virus and adenovirus) produced negative results with both substrates. Also, virus negative controls without virus were appropriately negative. These results clearly demonstrate the specificity of 4,7-dialkoxy-N-acetylneuraminic acid chromogenic substrates for influenza type A and B viruses.

EXAMPLE 4

Similar results as reported in Example 3 were obtained using 5-bromo-4-chloro-indol-3-ol and 4-methylumbelliferone as reporter molecules on 4-methoxy-Neu5Ac and 4,7-dimethoxy-Neu5Ac.

Numerous modifications and variations in practice of the invention are expected to occur to those skilled in the art upon consideration of the foregoing detailed description of the invention. Consequently, such modifications and variations are intended to be included within the scope of the following claims.

That which is claimed is:

1. A 4,7-dialkoxy-N-acetylneuraminic acid of the general formula wherein $R_1$ and $R_2$ are alkyl groups containing 1 to 4 carbon atoms.

2. A 4,7-dialkoxy-N-acetylneuraminic acid as defined in claim 1, wherein both $R_1$ and $R_2$ are methyl groups.

3. A 4,7-dialkoxy-N-acetylneuraminic acid as defined in claim 1, wherein both $R_1$ and $R_2$ are ethyl groups.

4. A 4,7-dialkoxy-N-acetylneuraminic acid substrate of the general formula wherein $R_1$ and $R_2$ are alkyl groups containing 1 to 4 carbon atoms and $R_3$ is a chromogenic or fluorogenic group.

5. A 4,7-dialkoxy-N-acetylneuraminic acid substrate as defined in claim 4, wherein both $R_1$ and $R_2$ are methyl groups and $R_3$ is a chromogenic group.

6. A 4,7-dialkoxy-N-acetylneuraminic acid substrate as defined in claim 5, wherein $R_3$ is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, and 6-bromo-2-naphthyl.

7. A 4,7-dialkoxy-N-acetylneuraminic acid substrate of the general formula:

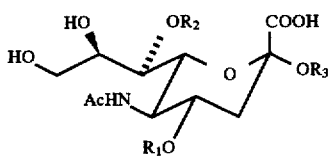

wherein both $R_1$ and $R_2$ are methyl groups and $R_3$ is 5-bromo-3-indolyl.

8. A 4,7-dialkoxy-N-acetylneuraminic acid substrate as defined in claim 4, wherein both $R_1$ and $R_2$ are ethyl groups and $R_3$ is a chromogenic group.

9. A 4,7-dialkoxy-N-acetylneuraminic acid substrate as defined in claim 8, wherein $R_3$ is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, and 6-bromo-2-naphthyl.

10. A method for detecting influenza type A and B viruses in a clinical sample from an individual suspected of having a respiratory viral infection, said method comprising:
(1) incubating the clinical sample with a chromogenic or fluorogenic 4,7-dialkoxy N-acetylneuraminic acid substrate of the general formula:

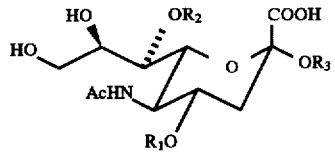

wherein $R_1$ and $R_2$ are alkyl radicals containing 1 to 4 carbon atoms and $R_3$ is a chromogenic or fluorogenic group that exhibits a distinct and characteristic color when cleaved from the substrate or a salt of the substrate;
(2) concentrating any precipitate formed in the incubated clinical sample;
(3) observing the concentrated precipitate to determine whether the distinct and characteristic color is formed, wherein the formation of the distinct and characteristic color indicates the presence of influenza type A or B viruses in the clinical sample.

11. A method as defined in claim 10, wherein both $R_1$ and $R_2$ are methyl groups and $R_3$ is a chromogenic group.

12. A method as defined in claim 11, wherein $R_3$ is selected from the group consisting of 4-methylumbelliferyl, 3-cyanoumbelliferyl, 2-nitrophenyl, 4-nitrophenyl, 3-resorufin, 5-bromo- 4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, and 6-bromo-2-naphthyl.

13. A method as defined in claim 12, wherein $R_3$ is 5-bromo-3-indolyl.

14. A method as defined in claim 10, wherein both $R_1$ and $R_2$ are ethyl groups and $R_3$ is a chromogenic group.

15. A method as defined in claim 14, wherein $R_3$ is selected from the group consisting of 4-methylumbelliferyl, 3-cyanoumbelliferyl, 2-nitrophenyl, 4-nitrophenyl, 3-resorufin, 5-bromo- 4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, and 6-bromo-2-naphthyl.

16. A method for detecting influenza type A and B viruses in a clinical sample from an individual suspected of having a respiratory viral infection, said method comprising:
(1) dividing the clinical sample into a first portion and a second portion;
(2) incubating the first portion with a chromogenic or fluorogenic 4,7-dialkoxy N-acetylneuraminic acid first substrate of the general formula:

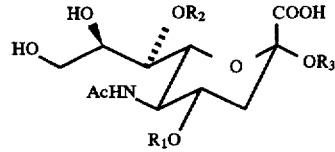

wherein $R_1$ and $R_2$ are alkyl radicals containing 1 to 4 carbon atoms and $R_3$ is a first chromogenic or fluorogenic group that exhibits a distinct and characteristic first color when cleaved from the first substrate or a salt of the first substrate;
(3) concentrating any precipitate formed in the incubated first portion;
(4) observing the precipitate formed in the incubated first portion to determine whether the distinct and characteristic first color is formed, wherein the formation of the distinct and characteristic first color indicates the presence of influenza type A or B viruses in the clinical sample;
(5) incubating the second portion with a chromogenic or fluorogenic 4-alkoxy N-acetylneuraminic acid second substrate of the general formula:

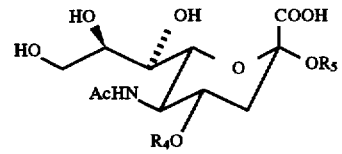

wherein $R_4$ is an alkyl radical containing 1 to 4 carbon atoms and $R_5$ is a second chromogenic or fluorogenic group that exhibits a distinct and characteristic second color when cleaved from the second substrate or a salt of the second substrate;
(6) concentrating any precipitate formed in the incubated second portion; and
(7) observing the precipitate formed in the incubated second portion to determine whether the distinct and characteristic second color is formed, wherein the formation of the distinct and characteristic second color indicates the presence of neuraminidase reactive viruses in the clinical sample;
wherein the presence of the first and second colors indicates the presence of influenza type A or B viruses alone or in combination with neuraminidase reactive viruses other than influenza type A and B viruses in the clinical sample;
wherein the presence of the second color and the absence of the first color indicates neuraminidase reactive viruses other than influenza type A and B viruses in the clinical sample; and
wherein the absence of the first and second colors indicates the absence of neuraminidase reactive viruses in the clinical sample.

17. A method as defined in claim 16, wherein both $R_1$ and $R_2$ are methyl groups and $R_3$ is a first chromogenic group.

18. A method as defined in claim 17, wherein $R_4$ is a methyl group and $R_5$ is a second chromogenic group.

19. A method as defined in claim 17, wherein $R_3$ and $R_4$ are independently selected from the group consisting of 4-methylumbelliferyl, 3-cyanoumbelliferyl, 2-nitrophenyl, 4-nitrophenyl, 3-resorufin, 5-bromo- 4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, and 6-bromo-2-naphthyl.

20. A method as defined in claim 19, wherein $R_3$ is 5-bromo-3-indolyl.

21. A method as defined in claim 18, wherein $R_3$ and $R_4$ are independently selected from the group consisting of 4-methylumbelliferyl, 3-cyanoumbelliferyl, 2-nitrophenyl, 4-nitrophenyl, 3-resorufin, 5-bromo- 4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, and 6-bromo-2-naphthyl.

* * * * *